United States Patent [19]

Bellin et al.

[11] Patent Number: 4,589,872
[45] Date of Patent: May 20, 1986

[54] QUICK ACTION FLOW REGULATOR FOR MEDICAL APPARATUS

[76] Inventors: Matthew E. Bellin, Burnsville, Minn.; Joseph A. Marino, Jr., Apple Valley, both of Minn.

[21] Appl. No.: 703,225

[22] Filed: Feb. 19, 1985

[51] Int. Cl.[4] ............................................. A61M 5/005
[52] U.S. Cl. ....................................... 604/246; 138/43; 251/215
[58] Field of Search ..................... 604/32, 33, 246–249, 604/241; 138/45, 46, 43; 251/122, 205, 215, 218, 319, 342, 145, 216

[56] References Cited

U.S. PATENT DOCUMENTS

| | | | |
|---|---|---|---|
| 2,926,409 | 3/1960 | Perry | 24/217 |
| 3,434,694 | 3/1969 | Skinner | 251/215 |
| 3,545,708 | 12/1978 | Gross | 248/74 |
| 3,840,209 | 10/1974 | James | 251/216 |
| 3,841,354 | 10/1974 | McDonnell | 138/43 |
| 3,868,973 | 3/1975 | Bierman et al. | 138/43 |
| 4,240,424 | 12/1980 | Akhavi | 604/241 |
| 4,240,428 | 12/1980 | Akhavi | 604/241 |
| 4,299,520 | 11/1981 | Iwata | 411/437 |
| 4,418,888 | 12/1983 | Jacobson et al. | 251/216 |
| 4,431,009 | 2/1984 | Marino, Jr. et al. | 128/673 |
| 4,432,762 | 2/1984 | Dawe | 604/253 |
| 4,435,111 | 3/1984 | Mizusawa | 411/437 |

FOREIGN PATENT DOCUMENTS

| | | | |
|---|---|---|---|
| 2726702 | 1/1979 | Fed. Rep. of Germany | 251/216 |
| 2131522 | 6/1984 | United Kingdom | 251/216 |

OTHER PUBLICATIONS

Renken, IBM Technical Disclosure Bulletin, vol. 17, No. 11, Apr. 1975.

Primary Examiner—John D. Yasko
Assistant Examiner—Jerome R. Smith, Jr.
Attorney, Agent, or Firm—Kinney & Lange

[57] ABSTRACT

A flow regulator for use in medical apparatus for quickly adjusting the flow of fluid in which there are coacting male and female threads for adjusting the position of the flow regulating device, a female threaded portion being yieldable. The position of the flow regulating device can be rapidly changed in either direction by exerting pressure on the valve stem to force the yieldable threaded portion outwardly to enable the threads of the male portion to pass over the threads of the female portion. The portion of the flow regulating device can be adjusted more precisely by turning the valve stem in the conventional manner to cause forward or reverse movement of the flow regulating device. The yieldable female threaded portion can either be integral with the main valve body but yieldable with respect thereto, or the yieldable portion may be a separate member yieldably secured to the main valve body by a spring clip or by an elastic band. Sealing means is disposed between the flow regulating device and the threaded portions to prevent the escape of fluid through the threaded portions.

The provision of such a yieldable female threaded portion which extends only over a portion of the periphery of the valve body not only has the advantage of enabling quick adjustment of the flow regulating device, but it also enables the valve body to be molded more readily.

11 Claims, 9 Drawing Figures

QUICK ACTION FLOW REGULATOR FOR MEDICAL APPARATUS

BACKGROUND OF THE INVENTION

1. Field of the Invention.

The present invention is concerned with a device for regulating the flow of fluid in medical apparatus in which there is means for quickly adjusting the position of the flow regulating device.

2. Description of the Prior Art.

There are many applications of medical equipment in which it is necessary to adjust the flow of fluid. The adjusting means not only has to be relatively compact, but it is also highly desirable that it be capable of being adjusted quickly until the approximate flow regulating position is obtained, and thereafter adjusted very finely to obtain exactly the right adjustment. A typical application is in connection with intravenous feeding in which the fluid from a container designed to hold intravenous fluid is connected by a tube or other flexible conduit to means for introducing the fluid into the patient. Any means for regulating the flow of such fluid must be very compact and must be capable of quickly adjusting the flow of fluid. It also must be capable of adjusting it in very small increments so that the flow rate is exactly what is desired.

One way of adjusting flow of fluid in such apparatus is through the use of a conventional roller flow control clamp. This is referred to in the Dawe U.S. Pat. No. 4,432,762. The difficulty with this type of arrangement is that it is very difficult to effect accurate adjustment as there is a great tendency for the adjustment to shift once it has been set.

This problem is recognized in the McDonnell U.S. Pat. No. 3,841,354 in which there is a male member in threaded connection with a female member, the threads of the male member being less in height than the depth of the grooves in the female member so that there is a passage between the male and female members. McDonnell suggests varying the depth of the grooves to provide further adjustment. In such a case, the fluid travels helically in the space between the threads. McDonnell is specifically concerned with an arrangement for adjusting the flow of intravenous fluids. The McDonnell device is, however, of a type which requires relatively slow adjustment and, if one wishes to make a major adjustment of the rate of flow, it is necessary to move the valve member through a large number of turns.

In the fastener art, arrangements have been proposed for having a yieldable female member which permits the nut to be rapidly tightened until it is in its approximate position. Thereafter, the screw or cooperating nut are relatively rotated to tighten them up. A typical device of this type is shown in the Mizusawa U.S. Pat. No. 4,435,111. In this patent, there are thread-like members formed on three yieldable portions. These are formed in the nut and enable the nut to be quickly tightened. It is always possible, after the nut is in a relatively tight position, for additional tightening to be accomplished by relative turning of the nut and the bolt. There is no way, however, of quickly releasing the nut. It must be unscrewed as with a conventional nut. The threads are formed so that if an attempt is made to pull the nut off, the threads will not release. Furthermore, the arrangement of this patent is completely unsuitable for an arrangement such as a valve where it is necessary to seal against escape of fluid.

The Perry U.S. Pat. No. 2,926,409 shows a fastening device in which it is possible to pull the elements apart after they have been fastened. The device does not have screw threads, however, and there is no provision for fine adjustment.

The Gross U.S. Pat. No. 3,545,708 shows a fastner in which there is a yieldable member which engages helical threads of a stud. The device to which the yieldable member is attached can be withdrawn, particularly if the yieldable member is bent downwardly. There is no concept, however, of having fine threaded engagement.

The Iwata U.S. Pat. No. 4,299,520 shows another fastener in which it is possible to slip the nut on but in which it cannot be removed except by unthreading it.

None of the patents referred to above are expressly adapted to the use of a flow regulating device in which it is desired to quickly adjust the flow in either direction and thereafter to adjust it in small increments.

SUMMARY OF THE INVENTION

The present invention is concerned with a flow regulator for use in medical apparatus in which flow of fluid can be quickly adjusted in either direction and can thereafter be adjusted more precisely.

The invention involves a flow regulating device in which there are male and female threads, and in which there is a female threaded portion that is yieldable. The position of the flow regulating device can be quickly changed in either direction by exerting pressure on the valve stem. Thereafter, the position of the valve of the flow regulating device can be adjusted more precisely by turning the valve stem in the conventional manner to cause forward or reverse movement of the flow regulating device.

The yieldable female threaded portion can either be integral with the main valve body but yieldable with respect thereto, or the yieldable portion may be a separate member yieldably secured to the main valve body by a spring clip or an elastic band.

Sealing means is disposed between the flow regulating device and the threaded portions to prevent the escape of fluid through the threaded portions.

The device, including the female threaded portion, is preferably molded, and the provision of threads only over a portion of the female threaded part enables the molding to be accomplished more readily.

Other objects of the invention will be apparent from the accompanying description, specification and drawing.

BRIEF DESCRIPTION OF THE DRAWINGS

FIG. 3 is a longitudinal sectional view of the position adjusting portion of a modified form of the flow regulating device of FIGS. 1, 2 and 2a.

DETAILED DESCRIPTION OF THE PREFERRED EMBODIMENTS

Figure 1:
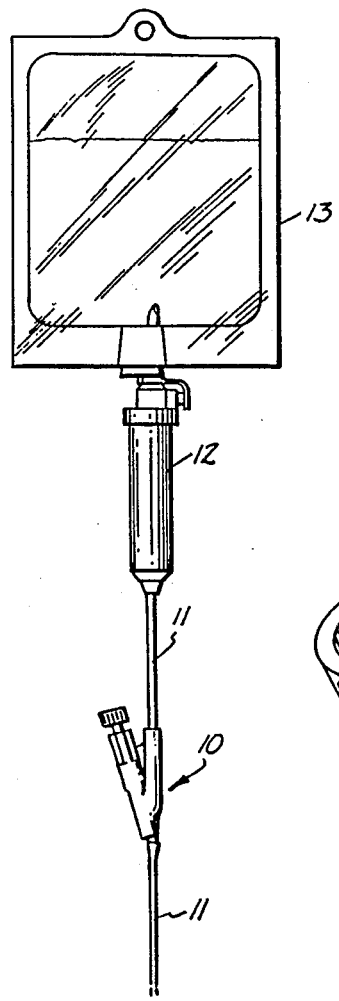
FIG. 1 is a view showing the improved flow regulating device connected in the tubing leading from a bag containing an intravenous fluid.

Referring to the drawing, the numeral 10 is employed to generally indicate the flow regulating device of the present invention. It will be noted that this is connected to tube 11 which is connected through the usual drip counter 12 to a container 13 which may contain a suitable intravenous fluid.

Figure 2:
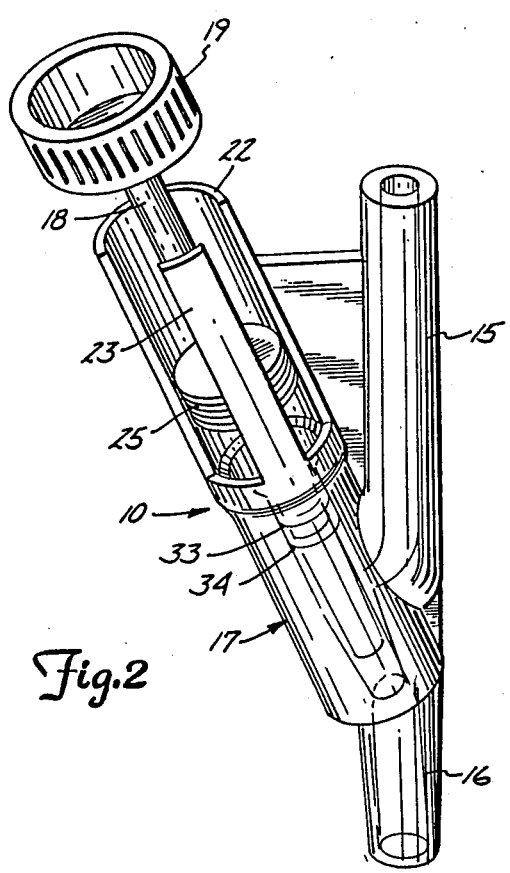
FIG. 2 is a perspective view of the improved flow regulating device.
Figure 7:
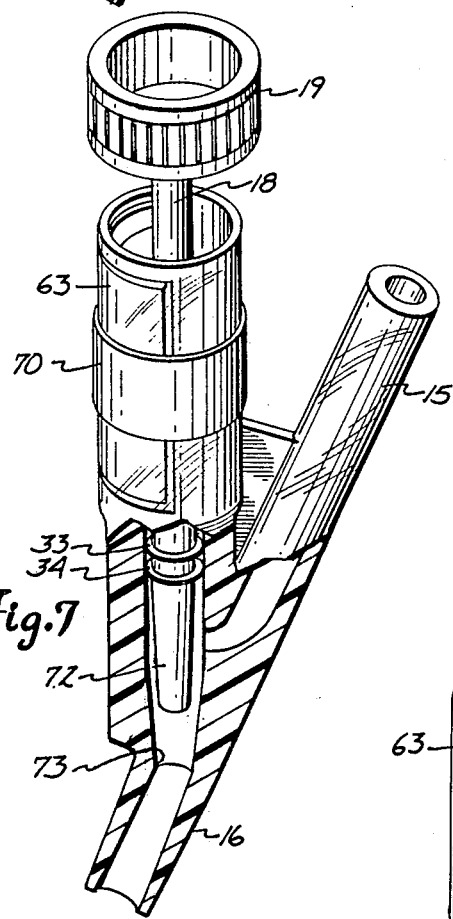
FIG. 7 is a view of a complete flow regulating device showing the valve and in which a separate yieldable threaded member is held in position by a yieldable band.

Referring to FIG. 2, the flow regulating device is provided with a tubular intake member 15 which connects to the portion of the tube 11 leading to the drip counter 12. The flow regulating device is also provided with a tubular outlet member 16 which connects to the portion of the tube 11 leading to the device for administering the fluid to the body. This may take the form of a hypodermic needle (not shown). A flow regulating member is located in the flow regulating device between the inlet and outlet tubular members 15 and 16, and may take any of various forms, but is shown in the modification of FIG. 7 as a tapered, conical valve. The flow regulating member or valve is adjusted by a stem 18 to which is secured a knob 19.

Figure 2A:
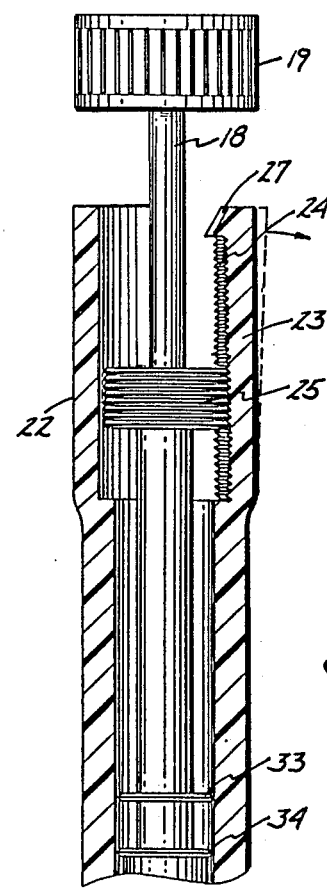
FIG. 2a is a longitudinal sectional view of the position adjusting portion of the flow regulating device of FIGS. 1 and 2.

It will be noted that the valve stem extends into a housing 17. This housing is a basically cylindrical housing having a lower portion in which is disposed the flow regulating member or valve. The upper portion of the housing 17 has a portion 22 cylindrical in shape but extending only partially around the circumference of the housing, as best seen in FIG. 2. As will be noted in FIG. 2, this portion has no internal threads. The upper portion of the housing also has an upstanding, cylindrically curved member 23 which is internally threaded, as at 24, as best shown in FIG. 2a. The stem 18 is provided with a collar 25 which has external threads engaging internal threads 24 of the cylindrically curved portion 23. As will be best seen in FIG. 2, the cylindrical internally threaded portion 23 is in the form of an arm which extends upwardly from a central portion 25 of the housing to the top of the housing. Normally the threaded collar 25 is in engagement with the threads 24, and by rotation of the knob 19, the stem 18 can be moved up or down. The threaded arm, while integral with the main body, is slightly yieldable and if sufficient force is applied to the knob 19, the stem 18 can be forced downwardly or upwardly by the threads of the threaded collar 25 slipping over the threads 24 of the threaded arm 23. As will be explained, this enables rather quick adjustment of the flow regulating member.

The flow regulating member can take any of various forms, as far as the present invention is concerned. As stated previously, the flow regulating member may take the form of a conical valve, such as shown in the modification of FIG. 7. It is to be understood that such a valve may be secured to the stem in any of the modifications.

It is very important that a seal be provided between the valve and the upper portion of the housing 17. It will be noted that the upper portion of housing 17 is open to the gap between the upstanding arm 23 of the cylindrical portion 22. Escape of fluid is prevented by a pair of sealing rings 33 and 34, best shown in FIG. 2a, although shown in phantom in FIG. 2. These sealing rings 33 and 34 prevent the escape of any fluid from the valve chamber out through the upper portion of the housing between portions 22 and 23.

The resilient arm 23 is preferably provided with an inwardly directed shoulder 27 at the upper end. If the stem 18 is pulled out rapidly to make a quick adjustment of the flow, the shoulder 27 will limit the outward movement of the stem by reason of the threaded collar engaging the shoulder 27. If it is desired to dissassemble the unit, the resilient arm 23 can be bent outwardly sufficiently to permit the threaded collar 25 to pass beyond the inwardly directed shoulder 27.

The advantage of being able to make a very rapid change in the fluid flow with relatively small movement of the stem 18 is very important in connection with the medical field. It is highly desirable that the rate of flow can be quickly adjusted. At the same time, it is also equally important that, as in the present device, it is possible to quickly move the flow regulating device to obtain approximately the desired flow and thereafter to make a very fine adjustment by simple rotation of the knob 19.

MODIFICATION OF FIGS. 3 AND 4

Figure 3:
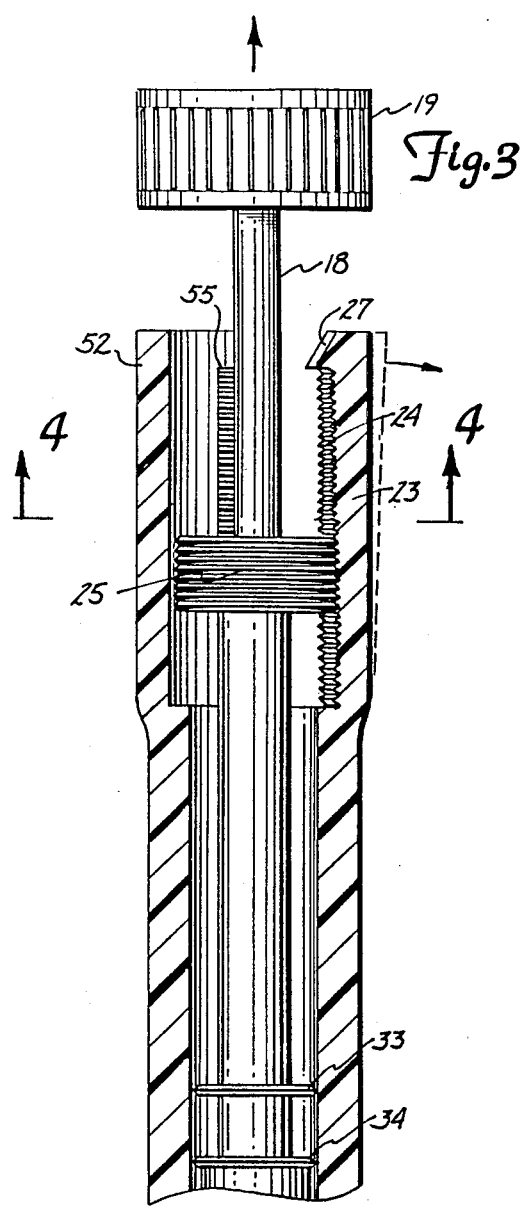
Figure 4:
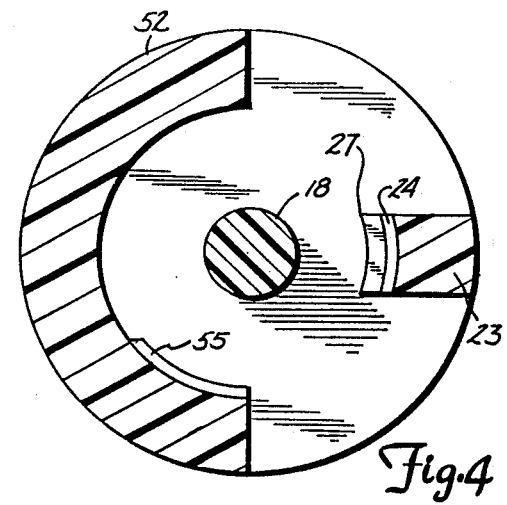
FIG. 4 is a cross-sectional view taken along line 4—4 of FIG. 3 and in the direction of the arrows adjacent that line.

The modification of FIGS. 3 and 4 is similar to that of FIGS. 1 through 2a, with the exception that threads are not only present on the upstanding resilient arm of the valve body, but are also present over a portion of the cylindrically curved portion facing the threaded arm.

In order to enable a ready comparison of the modification of FIGS. 3 and 4 with that of FIGS. 1 through 2a, the same numerals have been applied to elements which are unchanged. For those elements which correspond to elements in FIGS. 1 through 2a, but have been modified, a reference numeral 30 higher has been applied. Thus, the resilient portion 23, which is unmodified, is designated by the same numeral. The oppositely facing curved portion of the housing is designated in FIGS. 3 and 4 by the reference numeral 52. It will be noted from FIG. 3, that this portion has threads 55 extending over part of the inner periphery of the curved portion 52. The threads 55 are coextensive longitudinally with the threads 24 of the yieldable member 23. The cylindrical relationship between the threads 55 and the threads 24 is shown in the sectional view of FIG. 4. The threads 55 are naturally of the same pitch as threads 24, and are designed to coact with the threaded collar 25. The advantage of the arrangment of FIGS. 3 and 4 is that there is a more positive engagement of the coacting threaded portions, since the threads of the collar 25 are in engagement not only with the threads 24, but also with the threads 55 of a member which is relatively rigid and which does not flex as does the threaded portion 23. It is still possible, however, to move the stem 18 longitudinally by exerting enough force to spring the portion 23 outwardly enough to permit the threads of threaded collar 25 to ride not only over the threads 24, but also over the threads 55.

It is thus possible to rapidly adjust the valve or other flow regulating member by exerting pressure on the knob 19 to move collar 25 either up or down and then to make fine adjustments of the position of the flow regulating member by rotation of knob 19.

Figure 5:
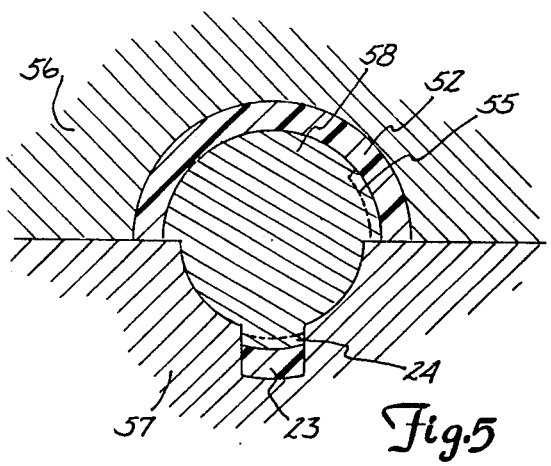
FIG. 5 is a cross-sectional view of the mold used in molding the device shown in FIGS. 3 and 4.

In both of the devices of FIGS. 1 through 2a and that of FIGS. 3 and 4, it is possible to readily mold the threads. This molding operation is shown in FIG. 5 in which a portion of the mold is shown in section. The mold is shown as having two opposed sections 56 and 57 and a center core 58. The center core 58 is formed with thread-like ridges designed to form the threads 55 and 24. The mold is also shaped to produce the cylindrical curved portion 52 as well as the resilient portion 23. With the molded sections 56 and 57 and the core 58 in the position shown, if plastic is injected into the mold, the mold is so shaped as to form the curved portion 52 along with the threads 55 and the curved portion 23 along with the threads 24. After the molding operation is completed, it is possible by, withdrawing the mold section 57, to rotate the core 58 in a counter-clockwise direction (as viewed in FIG. 5) to move the threaded portions of the core forming the threads 24 and 55 out of engagement with threads 24 and 55. It is now possible to readily withdraw the core 58 from the valve housing 17 and the mold. The valve housing 17 can now be withdrawn from the mold. If the threads extended over a substantial portion of the periphery of the core 58, this would not be possible. As it is, a rotation of less than 45° will free the core as far as both threads 24 and 55 are concerned to permit the core and the valve housing to be withdrawn.

It will thus be seen that the arrangement of the persent invention not only facilitates quick adjustment of the flow regulating member, but also enables the molded part to be readily withdrawn from the mold.

MODIFICATION OF FIG. 6

Figure 6:
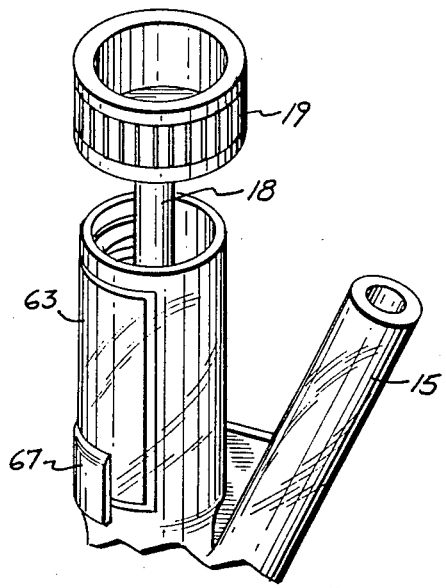
FIG. 6 is a fragmentary external view of the adjusting mechanism in which the yieldable threaded member is separate from the main valve body, but is yieldably secured in place by a clip.

Referring to FIG. 6, the same numerals have again been applied to elements which are unchanged from the corresponding elements in the modifications of FIGS. 1 through 4. Where the elements correspond to, but are different from, corresponding elements of the previous species, they have been assigned numbers 40 higher.

In the modification of FIG. 6, the yieldable threaded portion is in the form of a separate arcuate member 63, having threads formed over the interior thereof. The arcuate member should extend for no more than 180°. In connection with a slightly different modification, the arcuate member 63 is shown in more detail in FIG. 8. This member 63, with its internal threads 64, can be readily molded separately from the rest of the valve housing. It is retained in position in engagement with the threads of the threaded collar 25 by some resilient means. In the case of FIG. 6, the member 63 is held in position by a spring clip 67. The device may be provided with two such spring clips, one at the lower end and one at the upper end.

It will be readily apparent that if sufficient longitudinal thrust is placed upon the stem 18 through the knob 19, the threaded member 63 can spring outwardly against the resiliency of the clips 67, permitting rapid adjustment. Thereafter, the knob 19 can be rotated to make fine adjustments.

MODIFICATION OF FIGS. 7 AND 8

In FIG. 7 I have shown a complete valve unit, including the flow regulating member. In this case, the separate threaded member 23 is held in position by a resilient band 70 which completely encircles the valve body. Thus, as in FIG. 6, the threaded arcuate portion 23 can be pushed outwardly upon sufficient longitudinal force being applied to stem 18. This again enables the threads of the threaded collar 25 to pass by the threads 64 of the member 63.

In FIG. 7, I have shown a flow regulating device in the form of a needle valve 72, which cooperates with a conical seat 73. The needle valve is disposed between the inlet and outlet connections 15 and 16.

It is of course understood that a suitable sealing means such as the sealing rings 33 and 34 will be interposed between the needle valve 72 and the portion of the housing in which the yieldable threaded member 63 is disposed.

Figure 8:
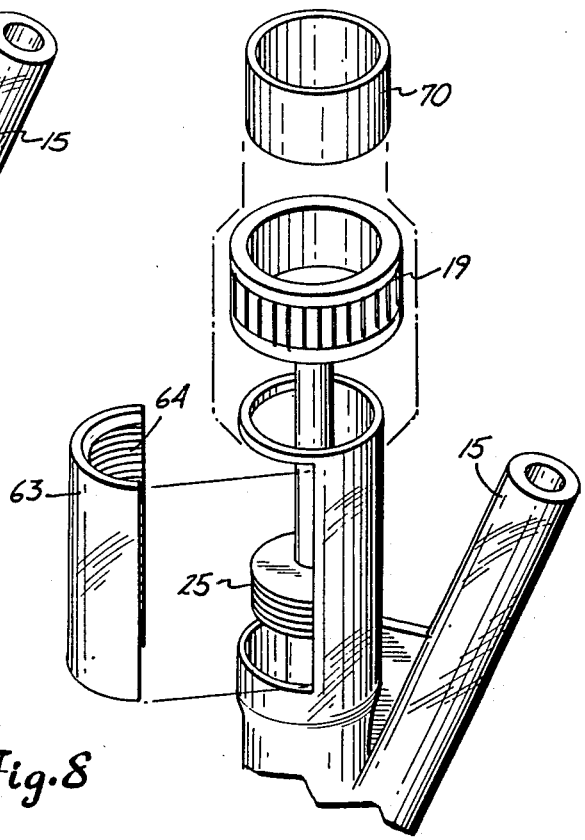
FIG. 8 is a fragmentary view of the modification of FIG. 7 with the parts being shown in exploded fashion.

In FIG. 8, I have shown the elements in exploded position. In assembling the unit, the threaded partially cylindrical member 63 will be placed in position. The elastic band 70 will then be stretched sufficiently to go over the knob 19 and over the housing to hold the threaded portion 63 in thread-engaging position with the threaded collar 25.

This modification, like that of the others, enables the operator to rapidly adjust the position of the valve or other flow regulating device and thereafter to adjust it finely.

CONCLUSIONS

It will be seen that we have provided a flow regulating device in which it is possible to quickly make a very substantial adjustment of the flow by a longitudinal movement of the flow regulating member. Furthermore, the valve stem not only can be moved longitudinally to make quick adjustments, but it can be rotated to adjust the flow regulating device very finely.

While we have shown the yieldable portion as a female portion, it is to be understood that the female threads could be non-yieldable and that the yieldable threaded member could be a male member coacting with the female threads.

While we have shown certain specific embodiments of our invention, it is to be understood that this is for purposes of illustration only and that the scope of our invention is limited solely by that of the appended claims.

What is claimed is:

1. For use in restricting the flow of fluid in medical apparatus,
    a valve body having inlet and outlet openings and a valve seat therebetween, said valve body having a female threaded portion displaced from said inlet and outlet openings;
    a valve stem having external threads threadedly engaging the female threaded portion and having a valve member secured thereto and cooperating with a valve seat to control flow between said inlet and outlet openings, the position of said valve member with respect to said valve seat being normally varied by adjusting the threaded engagement between the valve stem and the threaded portion of the valve body;
    said female threaded portion having a fixed portion and a yieldable threaded portion so that the position of the valve member can be rapidly changed in either direction by exerting pressure on the valve stem to force the yieldable threaded portion outwardly to enable the threads of the male portion to pass over the threads of the female portion; and
    sealing means disposed between the threaded portion of the valve body and the inlet and outlet openings to seal against the escape of fluid through said female threaded portion.

2. The apparatus of claim 1 in which the yieldable portion is integral with but yieldable with respect to the valve body.

3. The apparatus of claim 1 in which the yieldable portion is a separate portion held in position with respect to the valve body by yieldable means.

4. The apparatus of claim 3 in which the yieldable means is in the form of yieldable clips which engages the yieldable portion and the fixed threaded portion to permit the yieldable portion to move outwardly upon lateral pressure being applied thereto.

5. The apparatus of claim 3 in which the yieldable means is in the form of an elastic band surrounding the valve body.

6. The apparatus of claim 1 in which the fixed portion is free of the threads and in which the only threads are on the yieldable portion.

7. The apparatus of claim 2 in which both the fixed portion and the yieldable portion are threaded and in which the threads of both the fixed threaded portion and the yieldable threaded portion each extend over less than ninety degrees of the circumferential extent of the female threaded portion and in which the two sets of threads are substantially spaced from each other.

8. The apparatus of claim 2 in which the yieldable portion is formed with an inwardly extending tongue to retain the valve stem against accidental withdrawal from the valve body.

9. For use in restricting the flow of fluid in medical apparatus,
- a valve body having inlet and outlet openings and a valve seat therebetween, said valve body having a female threaded portion displaced from said inlet and outlet openings;
- a valve stem having an external threaded portion threadedly engaging the female threaded portion and having a valve member secured thereto and cooperating with a valve seat to control flow between said inlet and outlet openings, the position of said valve member with respect to said valve seat being normally varied by adjusting the threaded engagement between the valve stem and the threaded portion of the valve body;
- one of said threaded portions being yieldable so that the position of the valve member can be rapidly changed in either direction by exerting pressure on the valve stem to flex the yieldable threaded portion to enable the threads of one of the threaded portions to pass over the threads of the other threaded portion; and
- sealing means disposed between the threaded portion of the valve body and the inlet and outlet openings to seal against the escape of fluid through said threaded portions.

10. In combination with a container for intravenous fluid for delivering fluid at a controlled rate to a patient, a flexible conduit extending from said container for delivery of said fluid, a valve in said conduit for adjusting the rate at which fluid is delivered, said valve comprising:
- a valve body having inlet and outlet openings and a valve seat therebetween, said valve body having a female threaded portion displaced from said inlet and outlet openings;
- a valve stem having internal threads readily engaging the female threaded portion and having a valve member secured thereto and cooperating with a valve seat to control flow between said inlet and outlet openings, the position of said valve member with respect to said valve seat being normally varied by adjusting the threaded engagement between the valve stem and the threaded portion of the valve body;
- said female threaded portion having a fixed portion and a yieldable threaded portion so that the position of the valve member can be rapidly changed by exerting pressure on the valve stem to force the yieldable threaded portion outwardly to enable the threads of the male portion to pass over the threads of the female portion to adjust quickly the flow of fluid from the container; and
- sealing means disposed between the threaded portion of the valve body and the inlet and outlet openings to seal against the escape of fluid through said female threaded portion.

11. The apparatus of claim 9 in which the flow passages through the inlet and outlet openings are aligned with each other to minimize the formation of air bubbles in the intravenous fluid and to facilitate the cleaning of the valve.

* * * * *